United States Patent [19]

Evans et al.

[11] 4,426,295

[45] Jan. 17, 1984

[54] CELL SUSPENSION CHAMBER PROCESS

[76] Inventors: Deborah A. Evans, 115 NW. 122 St., North Miami, Fla. 33168; Lisbeth E. Shelley, 7805 Camino Real, Apt. H301, Miami, Fla. 33143

[21] Appl. No.: 306,494

[22] Filed: Sep. 28, 1981

[51] Int. Cl.³ ............................................. B01D 37/00
[52] U.S. Cl. .................................... 210/772; 210/927
[58] Field of Search .............. 210/767, 805, 445, 446, 210/450, 453, 927, 772; 422/101

[56] References Cited

U.S. PATENT DOCUMENTS

| | | | |
|---|---|---|---|
| 3,360,128 | 12/1967 | Federline | 210/94 |
| 3,361,261 | 1/1968 | Fairey et al. | 210/445 |
| 3,640,388 | 2/1972 | Ferrari | 210/94 |
| 3,726,795 | 4/1973 | Edwards | 210/233 |
| 3,731,806 | 5/1973 | McCormick | 210/94 |
| 3,782,548 | 1/1974 | Bowen | 210/94 |
| 4,080,294 | 3/1978 | Edwards et al. | 210/232 |
| 4,115,277 | 9/1978 | Swank | 210/927 |
| 4,212,742 | 7/1980 | Solomon et al. | 210/247 |
| 4,267,276 | 5/1981 | Crawford et al. | 435/291 |
| 4,301,010 | 11/1981 | Eddleman et al. | 422/101 |

OTHER PUBLICATIONS

A Manual of Cytotechnology, 5th Ed., Pub. by American Society of Clinical Pathologists, pp. 280 and 310-311.

Evans and Shelley, Cytotechnologists Bulletin, XVII, (No. 5), pp. 79-80, Oct. 1, 1980.

Cytopreparation with Micro Slides and Membrane Filters, Am. Soc. of Clin. Path. and College of Am. Path., (Mar. 1976), pp. 7-10.

Plowden and Gill, Cytotechnologists Bulletin XII, No. 6, pp. 8-10, (1975).

Primary Examiner—Ivars C. Cintins
Attorney, Agent, or Firm—Irons and Sears

[57] ABSTRACT

A process is provided which permits the rapid concentration and collection of cells in body fluid with minimal need for centrifugation and without filtration or sediment flotation, while also permitting the collection of cells from the fluid in an essentially monolayer arrangement with essentially no cell distortion. The apparatus used in this process comprises an elongated receptacle or chamber having, at one end, an outlet opening through which body fluid containing cells to be collected can be introduced, e.g., by means of a syringe, and, interposed between the inlet opening and an outlet opening at the other end of the chamber, a filter, e.g., a microporous filter.

18 Claims, 6 Drawing Figures

CELL SUSPENSION CHAMBER PROCESS

BACKGROUND OF THE INVENTION

Heretofore the preparation of sero-sanguineous body cavity fluid specimens for cytologic microscopic evaluation has usually been a time consuming process and has frequently given rise to poor cell quality, thereby hindering complete cell evaluations. In a large part, these difficulties have resulted from the equipment used.

Present preparation techniques can take 45 minutes or longer to complete. In cases in which sparsely populated cytologic specimens are utilized, the process requires the processing of relatively large specimen samples, and multiple pieces of equipment with only a few cells being collected in each run. This requires the added and potentially cell distorting step of combining the various cell samples into one sample for evaluation. The present standard collection techniques are filtration and flotation processes and centrifugation methods.

The flotation process, which is a sedimentation process, is described in "A Manual of Cytotechnology ASCP (1977), pages 310-311. In the flotation process the cell, in its original solution or in a physiologic saline solution, is carefully layered over an albumin solution, having a specific gravity of 1.050 to 1.060, in a centrifuge tube. The tube is then centrifuged causing a separation of the cells, said separation being dependent upon the cell's specific gravity and the specific gravity of the albumin solution utilized. The overall process is time consuming and frequently results in poor cell recovery. The process is also limited by the size of the centrifuge tube leading, in many cases, to the use of multiple centrifuge tubes, and concomitantly many individual processes. The cells from the individual tubes must then be collected into one cell sample.

In the conventional centrifugation process, the body fluid, such as blood, is placed in an elongated tube, such as a test tube or a specifically designed centrifuge tube, and the tube subjected to a centrifugal force to separate the cells from the serum fraction. In this process the cells to be collected are forced to the bottom of the tube. The supernatant liquid is then removed and the cells resuspended. Utilizing a pipette, one to two drops of the cell suspension is then placed in a tube for the cytospin (cytocentrifuge) which is then centrifuged while the cells concomitantly are automatically placed on a microscopic slide in a compact circle. An absorbent paper against slide absorbs the liquid from the suspension. Unfortunately the absorbent will also absorb some of the cells thus decreasing the already small amount of cells which is available for deposition on the microscopic slide.

The cytospin can also be utilized in conjunction with the flotation process.

For the filtration process, there are numerous apparatuses and membrane filter materials on the market which perform adequately for the collection of cells. Unfortunately there are many pitfalls in the use of membrane filters and the collected cells, in many instances, are damaged and hence of little value for microscopic examinations.

Prior to the introduction of membrane filters, sparsely populated cytologic specimens contained so few cells that it was physically impossible to recover them and make cell spreads. This difficulty was essentially eliminated by the use of membrane filters. Membrane filters are in general made from cellulosic products or polycarbonates.

In the filtration process, sparsely populated specimens can be filtered directly but other more populated specimens should be centrifuged first, the supernatant removed and the cell concentrate resuspended. In this process the filtration is a vacuum filtration process which packs the cells against the filter thus possibly damaging the cells. Also, if the technician is inexperienced or insufficient attention is being paid to the process, it is possible for the system to be pulled dry, i.e., most, if not all, fluid is removed from the cells and filter thus drying the cells. This too will result in damaged cells.

Ideally, cells on a filter from the filtration process, should be randomly distributed on a monolayer, without overlapping.

The present invention involves an apparatus which combines the beneficial aspects of the flotation and filtration processes but eliminates the disadvantages associated with each process. Most importantly, the present invention provides a means for obtaining cells in an essentially monolayer arrangement and with essentially no distortion.

BRIEF DESCRIPTION OF THE INVENTION

In this invention a process, and an apparatus for carrying out said process, have been developed which permit the rapid concentration of cells in body fluid with minimal need for centrifugation and without filtration, or sediment flotation, thus eliminating the many disadvantages of these prior art processes. The apparatus and process also permit the collection of cells in an essentially monolayer arrangement and with essentially no cell distortion.

In accordance with this invention the apparatus comprises a chamber having, at one end, an opening through which serosanguineous body fluid, or other fluid containing the cells to be collected, is introduced to the chamber, e.g. via a syringe, and at the other end a microporous filter. In the process of this invention fluid is repeatedly introduced, in increments, into the chamber where most of the fluid, in each increment, is removed through the microporous filter. The cells to be collected concentrate mainly in that portion of the introduced fluid which remains in the chamber, but a small quantity of cells may collect on the filter. The cells are then backwashed, by aspiration, into the syringe. In this step, a hemolytic solution is introduced into the chamber and retained in the chamber, that is, the preponderance of the fluid does not pass through the microporous filter. The fluid is withdrawn into the syringe and then reintroduced into the chamber. This step is repeated several times. This step serves several purposes, such as the loosening of any cells which may have collected on the filter and, where a hemolytic solution is utilized, the hemolysis of any red blood cells which may be present in the fluid. Upon completion of hemolysis, the hemolysed material is rinsed from the chamber by repeating this procedure using physiologic saline. If desired, the concentrated specimen may be further processed by a cytocentrifuge.

A brief description of the cell suspension chamber and process appear in an article published in *Cytotechnologists Bulletin*, XVII (No. 5) 79-80 (Oct. 1, 1980) under applicants' names.

BRIEF DESCRIPTION OF DRAWINGS

Although the configuration of the apparatus of this invention may take various shapes, the preferred configuration is that illustrated in the following drawings.

DESCRIPTION OF ILLUSTRATED EMBODIMENTS

Figure 1:
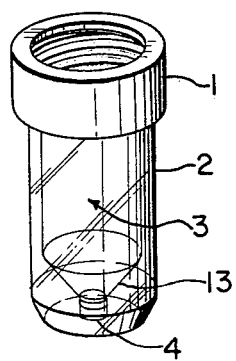
FIG. 1 is a view of the preferred assembled cell suspension chamber configuration of this invention.

As illustrated in FIG. 1 the cell suspension apparatus when fully assembled consists of two main portions, a cap portion 1 and a body portion 2, which is also referred to as the outer chamber 2, when chambers 2 and 3 are separate units. The interlocking means and filter means are not visible because they are held within cap 1. The chamber 2 is shown, in this embodiment, with an inner chamber 3, in which the concentration of the cells occurs. An opening 4 communicating with the inner chamber 3, is shaped to receive, in a sealed condition, the tip of an apparatus for introducing fluid into the chamber, such as a standard syringe.

The Figures illustrate the preferred embodiment for location of the opening into the inner chamber 3. The opening may also be positioned in other areas of the chamber, such as on the side. Openings in this area however, are not as efficient as the preferred location, as shown.

Figure 2:
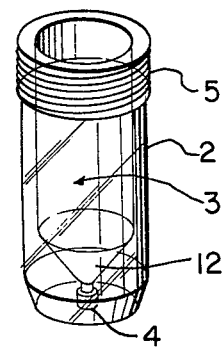
FIG. 2 is a view of the chamber body of FIG. 1 without the cap.

Chambers 2 and 3 may be separate chambers joined together at the top and bottom, as shown in FIG. 2, or they can be molded, as a single unit, from the same material, such as a polymeric material. If chambers 2 and 3 are separate units joined together, the space 13 between the chambers may be partially evacuated, or may contain air or some other gas, preferably an inert gas such as nitrogen and argon. Although not illustrated, inlet and outlet tubes can be easily attached to chamber 2 to provide a means for circulating a heat regulating fluid within space 13. This will permit the concentration of cells at higher or low temperatures than room temperatures.

The preferred embodiment is for chambers 2 and 3 to be molded as a single unit, that is, space 13 is eliminated. In this preferred embodiment the entire unit, chambers 2 and 3, closure means 5 and inlet 4, is molded as a single unit in one operation by standard molding procedures and chambers 2 and 3 together form a receptacle.

Chambers 2 and 3 may be formed from glass or synthetic polymers which are commercially available. If a synthetic polymer is selected, it (1) should be preferably transparent so that the operator can observe the material within the chamber 3 during the process; (2) must be inert to the body fluid or any reagent to be added to the chamber during the process; (3) should be resistant to impact damage; and (4) must be capable of being sterilized. Examples of synthetics which can be utilized include, but are not limited to, plexiglass, polycarbonates, acrylonitrile-butadiene-styrene, nylon, polyolefins, polyesters and polyimides. Some of these organopolymers can be heat sterilized whereas others must be sterilized by other means.

The capacity of chamber 2 is preferably about 5 cubic centimeters (cc)—although smaller or larger capacity can be utilized. For practical reasons an upper limit of about 20 cc has been adopted. This does not, however, eliminate the possibility of utilizing capacities greater than 20 cc. The dimensions for the screen given in the description will be based upon the preferred 5 cc capacity. Larger capacities may require larger screens and filters. Capacities less than 5 cc, although feasible, do not provide for efficient operation.

In FIG. 2 the details of the main body 2, are clearly evident. Starting at the top of the apparatus we find a means 5 for retaining the cap 1 on the chamber 2.

The outside diameter of the closure means should preferably be greater than the ouside diameter of chamber 2 which obviously is larger than the outside diameter of chamber 3. There is an opening 6 in the top of the closure means. The diameter of the opening 6 should be slightly less than the diameter of screens 7 and 9 and filter 8, which is preferably about 25 mm. This arrangement will ensure a tight seal between chamber 2 and cap 1.

Figure 6:
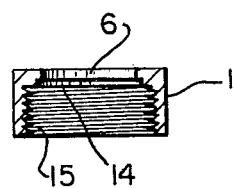
FIG. 6 is a cut away view of the cap of FIG. 3.

The cap 1 details are shown in FIG. 6. Cap 1, which is removably engageable with the body portion, is made preferably from a synthetic polymeric material which may be the same as or different from the polymeric material forming the body, having the same requirements as those for chamber 2 with the exception that it does not have to be transparent. The inside diameter of cap 1 should be sized to fit tightly to the outside of the closure means 5 and have a closure means 15 which cooperates with means 5. The top of cap 1 has an opening 6 whose diameter is preferably slightly less than the diameter of the screens 7 and 9 and filter 8, which are held against opening 6. The screens and filter are held, in the cap, within the space 14, by use of an O-ring 10 or other appropriate means. The lower edge of space 14 may form a lip to retain the screens, filter and O-ring and thus assist the O-ring in retaining the screens against opening 6. As illustrated in FIG. 6 the diameter of 14 is greater than opening 6 and approximately the same diameter as the screens.

Figure 3:
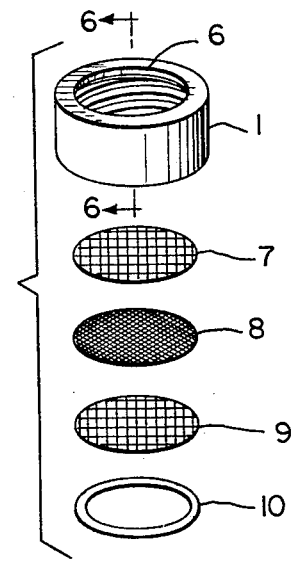
FIG. 3 is a breakaway view of the cap and its screen and filter components.

The arrangement of the screens 7 and 9 to the filter 8, O-ring 10 and cap 1 is illustrated in FIG. 3. The support screens are approximately 25 mm. in diameter and of relatively large mesh. The screens are mainly to support the filter 8 and not for the purpose of filtration. The screens can be stainless steel or synthetic polymeric material, having the same properties as the polymeric material for cap 1 or the main body. Such polymeric material need not be transparent. Filter 8 is a membrane filter, preferably made from cellulosic products or polycarbonates, approximately 25 mm. in diameter and of approximately 5.0 to 8.0 mm. pore size. During the cell concentration step the excess fluid passes through the filter concentrating the cells in the portion of fluid remaining in the chamber. Ideally few cells are collected on the filter during the process.

The gasket or O-ring 10 which holds the screens to the cap and seals the cap 1 to chamber 2 is prepared from rubber or a polymer. Gaskets for this purpose are commercially available.

Figure 4:
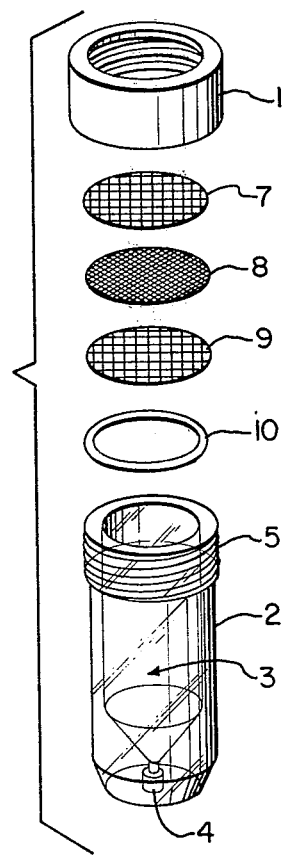
FIG. 4 is a breakaway view of the cap and chamber illustrating how the apparatus is assembled.

The cell suspension apparatus is assembled as shown in FIG. 4, which is a breakaway drawing showing the interrelation of each part.

Figure 5:
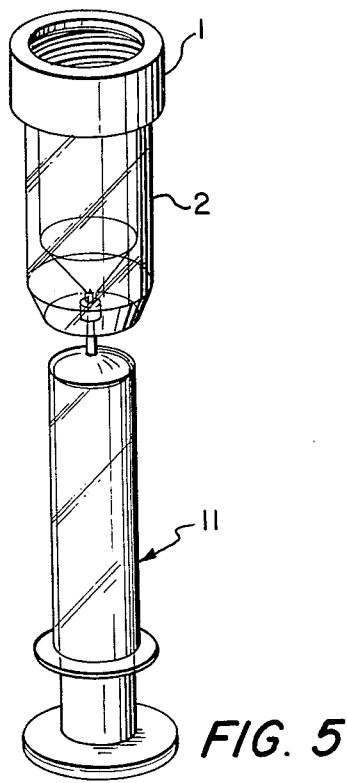
FIG. 5 is a view of the chamber in operation with a syringe as the fluid introducing means, connected to said chamber.

As an illustration of the utilization of the cell suspension apparatus, the apparatus is assembled, as in FIG. 4, with special care to the closure of cap 1 to chamber 2 to ensure a tight seal. A standard 20 cc. syringe is used to aspirate the sero-sanguineous specimen to be analyzed. The tip of the syringe is inserted in opening 4, as shown in FIG. 5, and the sero-sanguineous fluid transferred to chamber 3. Repeated fluid samples may be transferred until the resistance within the chamber builds to a tolerance level. This resistance is dependent upon the cellularity and amount of proteinaceous material in the specimen. The fluid should never be pressed into the chamber with excessive force as this will thrust the cells strongly against the screen 9 and filter 8, causing possible damage to the cells. The excess sero-sanguineous fluid from each sample passes through chamber 3, through the screens and filter and out opening 6.

The syringe 11 is then detached from the apparatus and two milliliters of a hemolytic solution is added to the syringe. During this operation little or no fluid escapes through opening 4 because of its small bore, which is approximately the same as the syringe or pipette opening. The syringe is then reattached to the apparatus and the solution introduced into chamber 3, and then withdrawn into the syringe and transferred back to the chamber. During this step, the hemolytic solution washes the filter to remove attached cells. The solution is essentially retained in the chamber and is not expelled from the chamber through the filter, as is the excess body fluid, until the hemolysis of the red blood cells has been completed. This hemolytic operation causes an immediate swelling of the red blood cells and provides a momentary hypotonic medium with a pH of approximately 4.5 to 5.0.

The specimen is then immediately rinsed with 5 to 10 ml. of physiologic saline (pH 5.5). Rinsing of the specimen prevents further lysis of leukocytes and epithelial cells and provides a clear fluid medium with a pH level of 5.5. Backwashing the specimen several times during this operation loosens cells which may have accumulated on the filter. The specimen may then be transferred to a test tube for further processing if needed.

In comparison studies, the epithelial tumor cell count in the chamber process was 542 cells in the cytocentrifuge (CCF) field for the sample as compared to 155 cells in the CCF field for the control. This comparison study shows that the cell yield utilizing the cell chamber is compatible with the routine process. The red blood count was zero in the chamber specimen and 445 in the control specimen. This lower red blood count provides less interference in viewing the resultant slide. The yield of diagnostic tumor cells of the comparison study showed a three-fold increase with a one-half preparation time.

While presently preferred embodiments of the inventions have been illustrated and described, it will be recognized that modifications may be made, and it is intended in the following claims to cover all such modifications which come within the spirit and scope of the invention.

What is claimed is:
1. A process for concentrating cells present in sero-sanguineous body fluids comprising:
  (a) introducing a sample of a serosanguineous body fluid, containing excess body fluid, into the elongated inner chamber of an apparatus comprising:
   (1) a body comprising:
    (i) an elongated inner chamber for receiving body fluids containing cells to be concentrated, said inner chamber being provided with an inlet opening at one end thereof through which body fluids can be introduced into said inner chamber, and an outlet opening at the opposite end of said inner chamber, and
    (ii) an outer chamber disposed about said inner chamber in spaced relationship thereto to form a housing for said inner chamber;
   (2) a cap portion removably engageable with said body portion at said outlet opening of said inner chamber, said cap portion having an opening therein communicating with said outlet opening of said inner chamber through which excess fluid within said inner chamber can be removed, and
   (3) a filter, interposed between said opening in said cap portion and said outlet opening in said inner chamber of said body portion, for retaining cells within said inner chamber while permitting excess fluid to be removed from said inner chamber, and permitting said excess body fluid to pass through said filter and be removed from said inner chamber, leaving a concentrated cell fluid in said inner chamber;
  (b) adding a hemolytic solution to said concentrated cell fluid in said inner chamber;
  (c) withdrawing and reintroducing the combined fluids from step (b) into said inner chamber at least once;
  (d) adding a physiologic saline solution to said combined fluids in said inner chamber, and
  (e) withdrawing and reintroducing into said inner chamber the combined fluids from step (d) at least once, during which process any cells on said filter are washed off into said combined fluids, the fluid remaining within said inner chamber being a concentrate solution of cells capable of being analyzed.

2. A process for concentrating cells present in sero-sanguineous body fluids as claimed in claim 1, wherein said hemolytic solution is a mixture of 4 parts physiologic saline and 1 part glacial acetic acid.

3. A process for concentrating cells present in sero-sanguineous body fluids as claimed in claim 1, wherein said inner chamber and said outer chamber of said body portion of said apparatus are cylindrical in shape, and wherein said outer chamber is coaxially disposed about said inner chamber.

4. A process for concentrating cells present in sero-sanguineous body fluids as claimed in claim 3, wherein said inlet opening of said inner chamber of said apparatus is adapted to support a syringe.

5. A process for concentrating cells present in sero-sanguineous body fluids as claimed in claim 4, wherein said syringe is a hypodermic syringe.

6. A process for concentrating cells present in sero-sanguineous body fluids as claimed in claim 3, wherein said filter is supported in said cap portion of said apparatus by screens.

7. A process for concentrating cells present in sero-sanguineous body fluids as claimed in claim 6, wherein said filter and said screens are retained in said cap portion of said apparatus by means of an O-ring.

8. A process for concentrating cells present in sero-sanguineous body fluids as claimed in claim 3, wherein the diameter of said opening in said cap portion of said apparatus is less than the diameter of said outlet opening of said body portion of said apparatus.

9. A process for concentrating cells present in serosanguineous body fluids as claimed in claim 3, wherein said cap portion of said apparatus is engaged with said body portion by means of screw threads.

10. A process for concentrating cells present in serosanguineous body fluids comprising:
  (a) introducing a sample of a serosanguineous body fluid, containing excess body fluid, into the elongated receptacle of an apparatus comprising:
    (1) an elongated receptacle having an inlet opening at one end thereof through which body fluids containing cells to be concentrated can be introduced into said receptacle, and an outlet opening at the opposite end thereof;
    (2) a cap portion removably engageable with said receptable at said outlet opening thereof, said cap portion having an opening therein communicating with said outlet opening for allowing excess fluid within said receptacle to be removed, and
    (3) a filter, interposed between said opening in said cap portion and said outlet opening in said receptacle, for retaining cells within said receptacle while permitting excess fluid to be removed from said receptacle, and permitting said excess body fluid to pass through said filter and be removed from said receptacle, leaving a concentrated cell fluid in said receptacle;
  (b) adding a hemolytic solution to said concentrated cell fluid in said receptacle;
  (c) withdrawing and reintroducing the combined fluids from step (b) into said receptacle at least once;
  (d) adding a physiologic saline solution to said combined fluids in said receptacle, and
  (e) withdrawing and reintroducing into said receptacle the combined fluids from step (d) at least once, during which process any cells on said filter are washed off into said combined fluids, the fluid remaining within said receptacle being a concentrate solution of cells capable of being analyzed.

11. A process for concentrating cells present in serosanguineous body fluids as claimed in claim 10, wherein said hemolytic solution is a mixture of 4 parts physiologic saline and 1 part glacial acetic acid.

12. A process for concentrating cells present in serosanguineous body fluids as claimed in claim 10, wherein said receptacle of said apparatus is cylindrical in shape.

13. A process for concentrating cells present in serosanguineous body fluids as claimed in claim 12, wherein said inlet opening of said apparatus is adapted to support a syringe.

14. A process for concentrating cells present in serosanguineous body fluids as claimed in claim 13, wherein said syringe is a hypodermic syringe.

15. A process for concentrating cells present in serosanguineous body fluids as claimed in claim 12, wherein said filter is supported in said cap portion of said apparatus by screens.

16. A process for concentrating cells present in serosanguineous body fluids as claimed in claim 15, wherein said filter and said screens are retained in said cap portion of said apparatus by means of an O-ring.

17. A process for concentrating cells present in serosanguineous body fluids as claimed in claim 2, wherein the diameter of said opening in said cap portion of said apparatus is less than the diameter of said outlet opening of said receptacle.

18. A process for concentrating cells present in serosanguineous body fluids as claimed in claim 12, wherein said cap portion of said apparatus is engaged with said receptacle by means of screw threads.

* * * * *

UNITED STATES PATENT AND TRADEMARK OFFICE
CERTIFICATE OF CORRECTION

PATENT NO. : 4,426,295

DATED : January 17, 1984

INVENTOR(S) : Deborah Ann Evans and Lisbeth Ellen Shelley

It is certified that error appears in the above-identified patent and that said Letters Patent is hereby corrected as shown below:

At column 1, line 23, a quotation mark --"-- should appear after "ASCP".

At column 2, line 16, "on" should be --as--.

At column 8, line 29 (claim 17), "2" should be --12--.

Signed and Sealed this

Seventeenth Day of July 1984

[SEAL]

*Attest:*

GERALD J. MOSSINGHOFF

*Attesting Officer*     *Commissioner of Patents and Trademarks*